(12) United States Patent
Tanabe

(10) Patent No.: US 11,703,491 B2
(45) Date of Patent: Jul. 18, 2023

(54) SENSOR MODULE

(71) Applicant: TDK Corporation, Tokyo (JP)

(72) Inventor: Kei Tanabe, Tokyo (JP)

(73) Assignee: TDK CORPORATION, Tokyo (JP)

( * ) Notice: Subject to any disclaimer, the term of this patent is extended or adjusted under 35 U.S.C. 154(b) by 0 days.

(21) Appl. No.: 17/360,063

(22) Filed: Jun. 28, 2021

(65) Prior Publication Data

US 2022/0018819 A1 Jan. 20, 2022

(30) Foreign Application Priority Data

Jul. 20, 2020 (JP) ................. 2020-123506

(51) Int. Cl.
*G01N 33/00* (2006.01)
*H05K 5/00* (2006.01)
(52) U.S. Cl.
CPC ......... *G01N 33/004* (2013.01); *H05K 5/0026* (2013.01)
(58) Field of Classification Search
CPC .................................................... G01N 33/004
USPC ....................................................... 73/31.01
See application file for complete search history.

(56) References Cited

U.S. PATENT DOCUMENTS

| 2007/0107493 | A1 | 5/2007 | Katsuda et al. | |
| 2017/0131230 | A1* | 5/2017 | Papageorge | ....... G01N 27/4045 |
| 2018/0100842 | A1 | 4/2018 | Ahn et al. | |
| 2019/0064093 | A1* | 2/2019 | Ura | ......... G01N 27/12 |
| 2019/0383761 | A1 | 12/2019 | Kimura et al. | |

FOREIGN PATENT DOCUMENTS

| JP | 4280705 B2 | 6/2009 |
| RU | 196983 U1 | 3/2020 |
| WO | 2004/111627 A1 | 12/2004 |

OTHER PUBLICATIONS

Jung et al. Machine Translation of WO 2020138591. Published Jul. 2020. Accessed Oct. 2022. (Year: 2020).*
Extended European Search Report issued in corresponding European Patent Application No. 21186325.3-1020, dated Nov. 26, 2021.
European Office Action issued in corresponding European Patent Application No. 21186325.3-1001, dated Oct. 11, 2022.

* cited by examiner

*Primary Examiner* — Walter L Lindsay, Jr.
*Assistant Examiner* — Philip T Fadul
(74) *Attorney, Agent, or Firm* — McDermott Will & Emery LLP

(57) ABSTRACT

Disclosed herein is a sensor module that includes a substrate having a top surface and a back surface, a sensor element mounted on the top surface of the substrate, an external terminal formed on the back surface of the substrate, and a case fixed to the substrate so as to cover the sensor element. The case has a top plate part having a plurality of through holes. The top plate part has a center area having no through holes and a through hole formation area having the plurality of through holes, the through hole formation area being positioned so as to surround the center area.

18 Claims, 15 Drawing Sheets

SENSOR MODULE

BACKGROUND OF THE INVENTION

Field of the Invention

The present invention relates to a sensor module and, more particularly, to a sensor module for detecting, e.g., a predetermined gas component contained in a measurement atmosphere.

Description of Related Art

A gas sensor for detecting a predetermined gas component is described in Japanese Patent No. 4,280,705. The gas sensor described in Japanese Patent No. 4,280,705 includes a substrate having a cavity, a gas detection element housed in the cavity, and a protective cap covering the cavity. The protective cap has a plurality of vent holes, through which an external gas to be measured is introduced into the cavity.

In the gas sensor described in Japanese Patent No. 4,280,705, the protective cap has, at its top, a planar portion having no vent hole. With the planar portion sucked by a suction nozzle of a chip mounter, the gas sensor is surface-mounted on a circuit board.

However, in the gas sensor described in Japanese Patent No. 4,280,705, the planar portion of the protective cap is formed eccentric to the center position, so that when it is sucked by the chip mounter suction nozzle, the posture of the gas sensor may become unstable. Such a problem may occur not only in the gas sensor but also in all the sensor modules that are surface-mountable on a circuit board, including, for example, sensor modules for detecting vibration, pressure, and temperature of air, which are specifically microphones, pressure sensors, and temperature sensors.

SUMMARY

It is therefore an object of the present invention, in a sensor module surface-mountable on a circuit board, to make the posture of the sensor module more stable during a sucking process using the chip mounter suction nozzle while ensuring sufficient air circulation.

A sensor module according to the present invention includes: a substrate having a top surface and a back surface; a sensor element mounted on the top surface of the substrate; an external terminal formed on the back surface of the substrate; and a case covering the sensor element fixed to the substrate. The case has a top plate part having a plurality of through holes. The top plate part has a center area having no through holes and a through hole formation area positioned so as to surround the center area and having the plurality of through holes.

According to the present invention, no through holes are formed in the center area of the top plate part, so that the center area can be sucked by a suction nozzle of a chip mounter, allowing the sensor module to be surface-mounted on a circuit board with a stable posture.

In the present invention, the top plate part may have a rectangular outer shape. This can maximize the volume of a space surrounded by the case. In this case, the through hole formation area may include a clearance area having no through holes, and the clearance area may be positioned in the vicinity of the corner portion of the top plate part or in the vicinity of substantially the center portion of the side of the top plate part. With this configuration, when the top plate part needs to be held with a jig in an inspection process, the clearance area can be held with the jig, thus preventing the through holes from being closed by the jig.

The sensor module according to the present invention may further include a filter overlapping the plurality of through holes. This can prevent foreign matters from entering the space surrounded by the case. In this case, the filter may selectively cover the through hole formation area so as to overlap the plurality of through holes without covering the center area. This can prevent contact between the filters and the suction nozzle during the suction process using the chip mounter suction nozzle.

Further, the filter may be formed as a single member having a continuous shape. This simplifies a filter attachment process and can enhance attachment strength between the filter and the top plate part. In this case, the top plate part may include an attachment area covered with the filter and a non-attachment area not covered with the filter, and the attachment area may overlap the through hole formation area, and the non-attachment area may include the center area, an outside area positioned outside the through hole formation area, and a separation area overlapping the through hole formation area and connecting the center area and the outside area. With this configuration, in a process of removing an unnecessary part of a filter sheet that has been attached to the top plate part, the unnecessary part that has been attached to the outside area and the unnecessary part that has been attached to the center area can be removed in a single step.

As described above, according to the present invention, it is possible to make the posture of the sensor module more stable during a suction process using the chip mounter suction nozzle while ensuring sufficient air circulation.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE EMBODIMENTS

Preferred embodiments of the present invention will be explained below in detail with reference to the accompanying drawings.

First Embodiment

Figure 1:
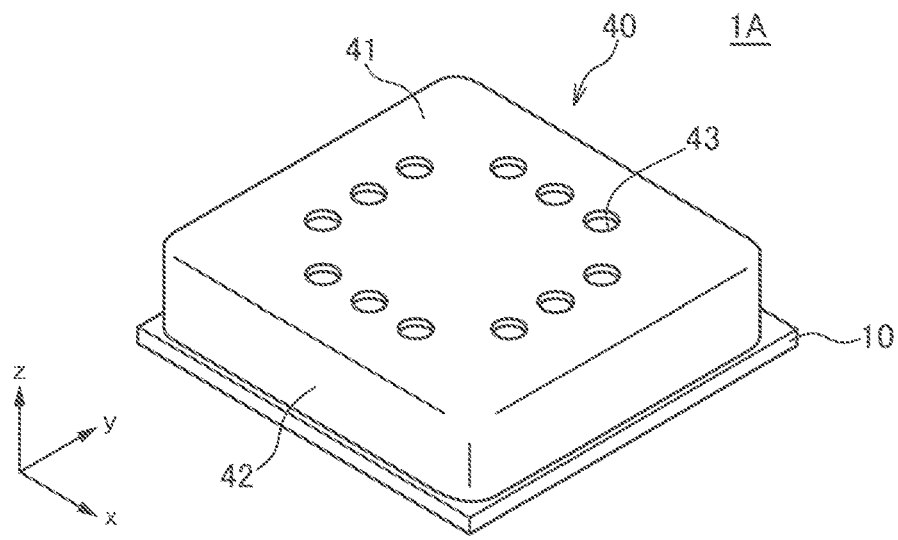
FIG. 1 is a schematic perspective view illustrating the outer appearance of a sensor module 1A according to a first embodiment of the present invention.
Figure 2:
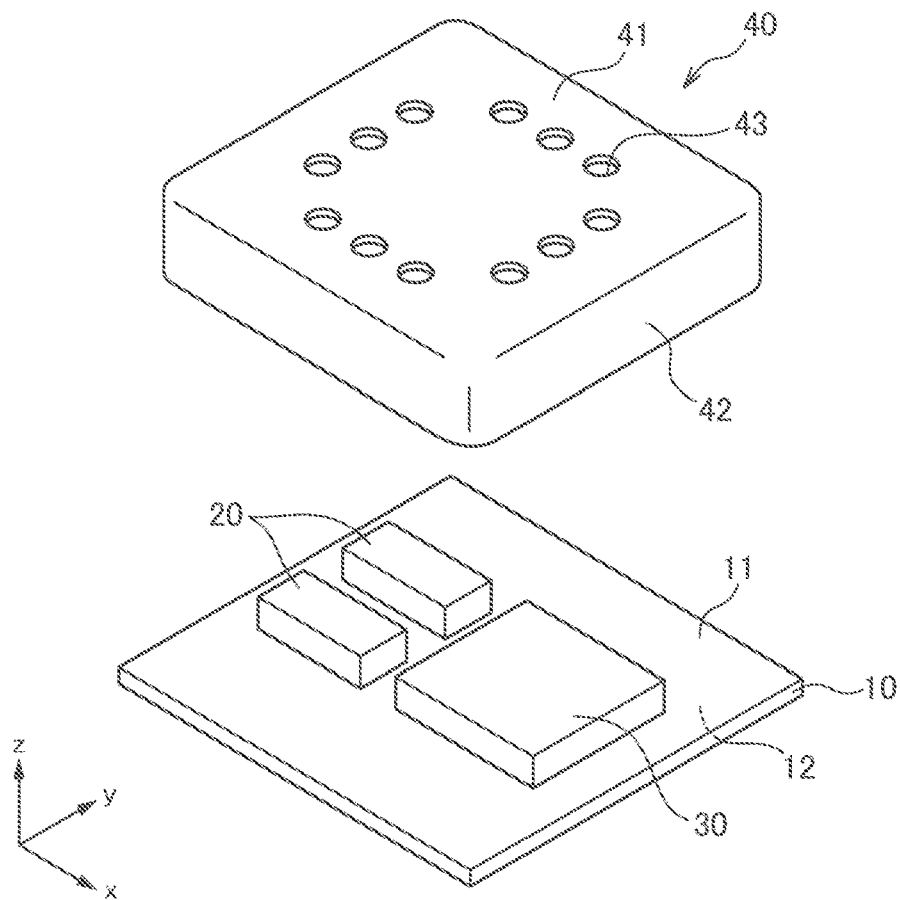
FIG. 2 is a schematic exploded view of the sensor module 1A.

FIG. 1 is a schematic perspective view illustrating the outer appearance of a sensor module 1A according to a first embodiment of the present invention. FIG. 2 is a schematic exploded view of the sensor module 1A.

Figure 3:
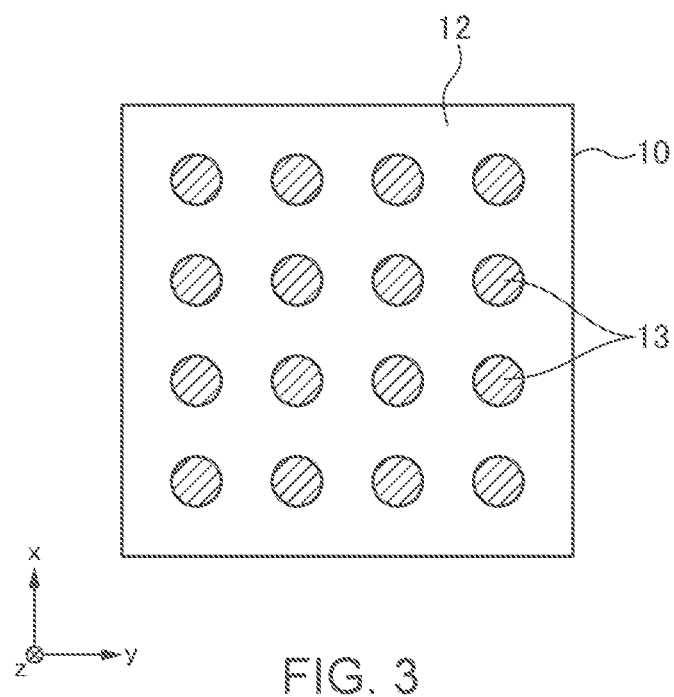
FIG. 3 is a schematic plan view of the sensor module 1A as viewed from a back surface.

As illustrated in FIGS. 1 and 2, the sensor module 1A according to the first embodiment includes a substrate 10, a sensor chip 20 and a control IC 30 which are mounted on a surface 11 of the substrate 10, and a case 40 which is fixed to the substrate 10 and covers the sensor chip 20 and control IC 30. As illustrated in FIG. 3, the substrate 10 has a plurality of external terminals 13 on aback surface 12 thereof. The surface 11 and back surface 12 of the substrate 10 constitute the xy plane.

The sensor chip 20 has a sensor element for measuring the concentration of a predetermined gas component ($CO_2$, etc.) contained in a measurement atmosphere. However, the sensor chip 20 may not necessarily be a gas sensor but may be a sensor for detecting vibration, pressure, temperature, humidity, or the like of the air in a measurement atmosphere, which is specifically, a microphone, a pressure sensor, a temperature sensor, a humidity sensor, or the like. In the example illustrated in FIG. 2, two sensor chips 20 are mounted on the substrate 10; however, the number of the sensor chips 20 to be mounted on the substrate 10 is not limited to a particular value.

The control IC 30 is connected to the sensor chip 20 and has an integrated control circuit for calculating measurement values based on the output from the sensor chip 20. Although not particularly limited, the control IC 30 may be a semiconductor IC in a bare-chip state. The control IC 30 is also connected to the external terminals 13. Some external terminals 13 may be connected directly to the sensor chip 20. The sensor chip 20 and the control IC 30 may not necessarily be separated chips, and an IC including a sensor element and a control circuit in one chip may be used.

The case 40 is made of a material having sufficient strength, such as metal or resin, and includes a top plate part 41 facing the surface 11 of the substrate 10 and a side plate part 42 connected to the top plate part 41 and surrounds the sensor chip 20 and control IC 30 in a plan view (as viewed in the z-direction). The top plate part 41 is parallel to the surface 11 of the substrate 10 and constitutes the xy plane. The side plate part 42 is perpendicular to the surface 11 of the substrate 10 and constitutes the xz plane or yz plane. The top plate part 41 has a plurality of through holes 43. The through holes 43 allow air to circulate therethrough from outside to inside of the case 40. For example, when the sensor chip 20 is a gas sensor, a gas component to be measured enters the inside of the case 40 through the through holes 43 and is measured in concentration by the sensor chip 20. In the present embodiment, the through hole 43 has a circular planar shape, which minimizes a reduction in strength of the top plate part 41 due to the presence of the through holes 43.

Figure 4:
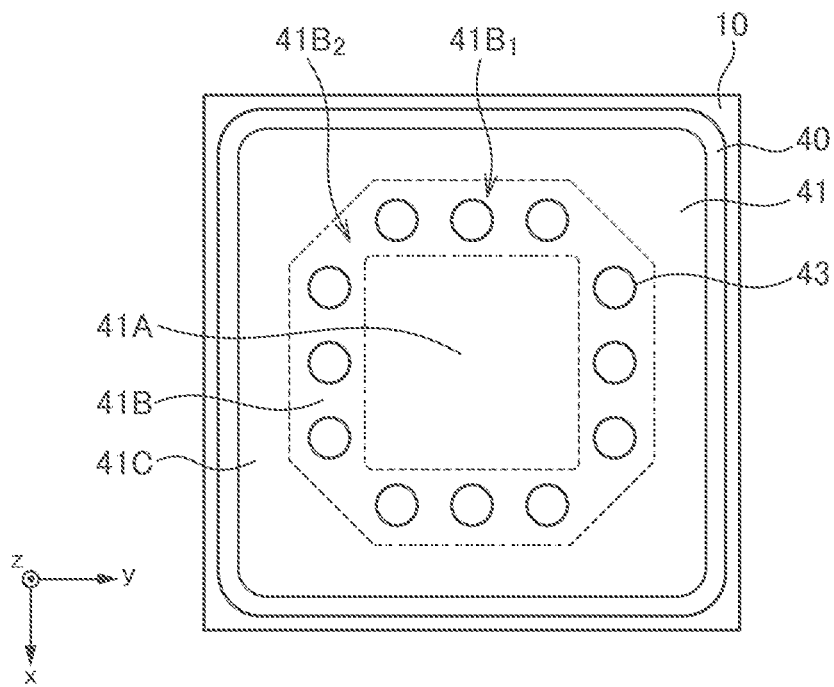
FIG. 4 is a schematic plan view for explaining the shape of the top plate part 41 in more detail.

FIG. 4 is a schematic plan view for explaining the shape of the top plate part 41 in more detail.

As illustrated in FIG. 4, the top plate part 41 has a rectangular planar shape and includes a center area 41A having no through holes 43, a through hole formation area 41B surrounding the center area 41A, and an outside area 41C positioned outside the through hole formation area 41B. The through holes 43 are all formed in the through hole formation area 41B. That is, the center area 41A and outside area 41C have no through holes 43. Some through holes 43 may overlap the sensor chip 20 or control IC 30 as viewed in the z-direction. The center position of the center area 41A coincides with the center position of the top plate part 41. The through hole formation area 41B has a ring shape and includes a linear part $41B_1$ in which three through holes 43 are arranged in the x-direction or y-direction and a corner part $41B_2$ connecting two linear parts $41B_1$. In the present embodiment, the corner part $41B_2$ is positioned in the vicinity of the corner portion of the top plate part 41 and constitutes a clearance area having no through holes 43.

Figure 5:
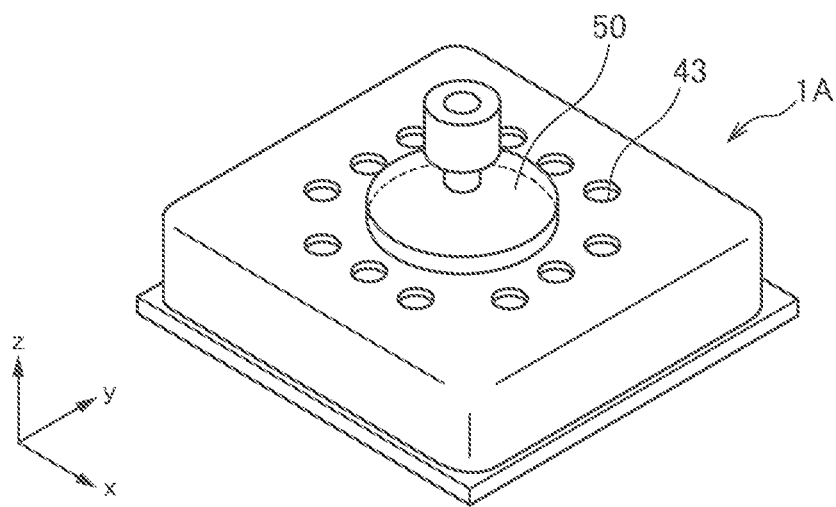
FIG. 5 is a schematic perspective view for explaining a conveying method for the sensor module 1A.

FIG. 5 is a schematic perspective view for explaining a conveying method for the sensor module 1A according to the present embodiment.

As illustrated in FIG. 5, when the sensor module 1A is conveyed, a suction nozzle 50 of a chip mounter is used to suck the center area 41A of the top plate part 41. As described above, no through holes 43 are formed in the center area 41A of the top plate part 41, thus allowing the center area 41A to be sucked reliably by the suction nozzle 50. Moreover, the planar position of the center area 41A of the top plate part 41 is not eccentric, so that the posture of the sensor module 1A in a state of being sucked by the suction nozzle 50 can be made more stable. As a result, it is possible to stably perform the work of surface-mounting the sensor module 1A on a not-shown circuit substrate.

Figure 6:
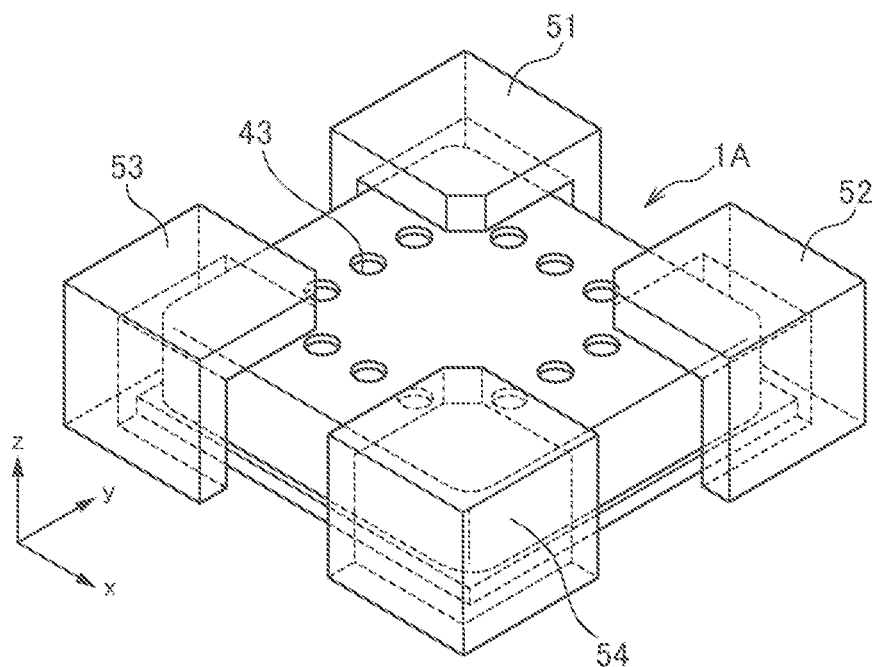
FIG. 6 is a schematic perspective view for explaining an inspection method for the sensor module 1A.

FIG. 6 is a schematic perspective view for explaining an inspection method for the sensor module 1A according to the present embodiment.

As illustrated in FIG. 6, in a process of inspecting the sensor module 1A according to the present embodiment, a not-shown probe is brought into contact with the external terminal 13 on the back surface 12 in a state where the top plate part 41 of the case 40 is held by a plurality of jigs 51 to 54. In this state, the concentration of a gas to be measured in the atmosphere is set to a known predetermined value, and it is determined whether a measurement value output from the external terminal 13 indicates a correct value, whereby screening of the sensor module 1A can be made.

The jigs 51 to 54 are disposed so as to cover the corner portions of the top plate part 41 and their vicinities. The corner portions and their vicinities are comparatively higher in strength against a force in the z-direction, thus preventing the sensor module 1A from being deformed and damaged during the inspection process. Although the jigs 51 to 54 are disposed so as to partially cover the through hole formation area 41B, they are disposed so as to each overlap the clearance area so as not to close the through hole 43. This allows the inspection to be performed under the same conditions as in actual use.

Second Embodiment

Figure 7:
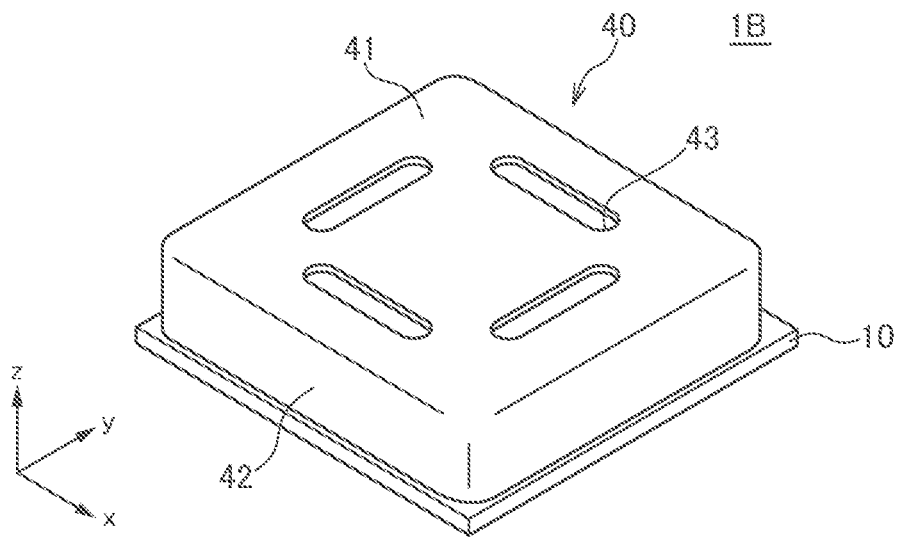
FIG. 7 is a schematic perspective view illustrating the outer appearance of a sensor module 1B according to a second embodiment of the present invention.

FIG. 7 is a schematic perspective view illustrating the outer appearance of a sensor module 1B according to a second embodiment of the present invention.

The sensor module 1B illustrated in FIG. 7 differs from the sensor module 1A according to the first embodiment in that the through hole 43 has a vertically or horizontally elongated shape. Other configurations are the same as those of the sensor module 1A according to the first embodiment, so the same reference numerals are given to the same elements, and overlapping description will be omitted. The through hole 43 in the present embodiment has a shape obtained by connecting three through holes 43 arranged in the x-direction or y-direction illustrated in FIG. 4. Using the through holes 43 having such a shape allows greater circulation of air from outside to inside of the case 40 while maintaining sufficient area of the center area 41A and outside area 41C.

Third Embodiment

Figure 8:
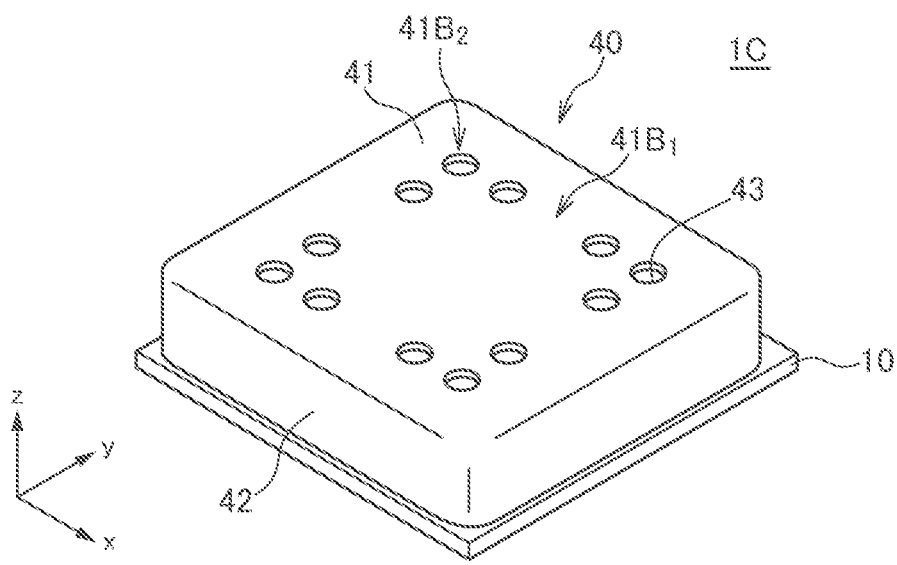
FIG. 8 is a schematic perspective view illustrating the outer appearance of a sensor module 1C according to a third embodiment of the present invention.

FIG. 8 is a schematic perspective view illustrating the outer appearance of a sensor module 1C according to a third embodiment of the present invention.

The sensor module 1C illustrated in FIG. 8 differs from the sensor module 1A according to the first embodiment in that three through holes 43 are arranged in an L-shape at the corner part $41B_2$ of the through hole formation area 41B. Other configurations are the same as those of the sensor module 1A according to the first embodiment, so the same reference numerals are given to the same elements, and overlapping description will be omitted. In the present embodiment, substantially the center portion of the linear part $41B_1$ constitutes the clearance area. The substantially center portion of the linear part $41B_1$ is positioned in the vicinity of substantially the center portion of the side of the top plate part 41. As exemplified in the present embodiment, the clearance area may not necessarily be provided at the corner part $41B_2$. Even with the configuration according to the present embodiment, it is possible to perform the inspection without closing the through holes 43 by holding the clearance areas with the jigs 51 to 54.

Fourth Embodiment

Figure 9:
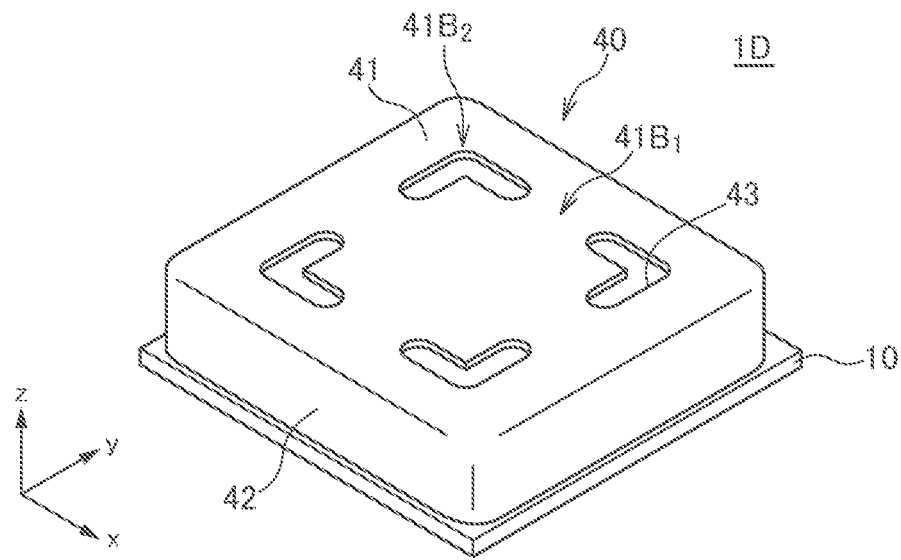
FIG. 9 is a schematic perspective view illustrating the outer appearance of a sensor module 1D according to a fourth embodiment of the present invention.
Figure 10:
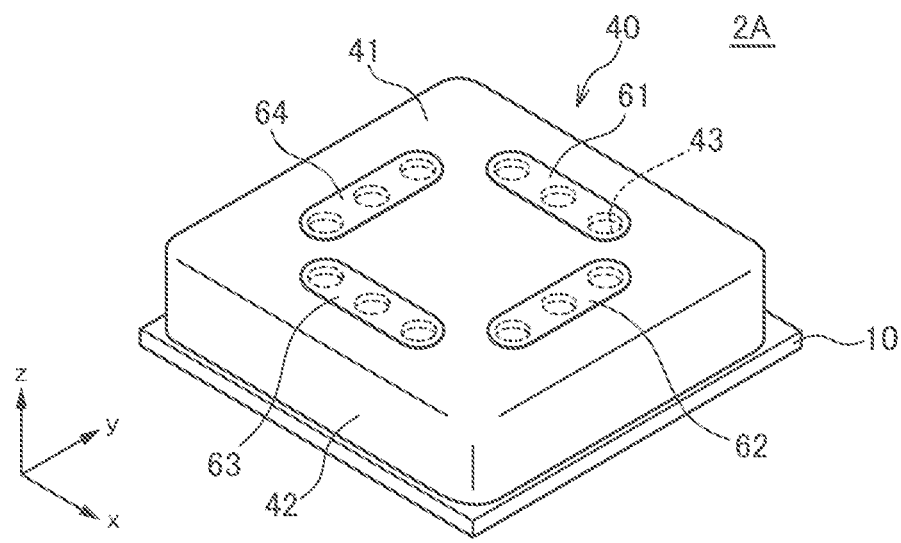
FIG. 10 is a schematic perspective view illustrating the outer appearances of sensor module 2A according to a fifth embodiment of the present invention.
Figure 11:
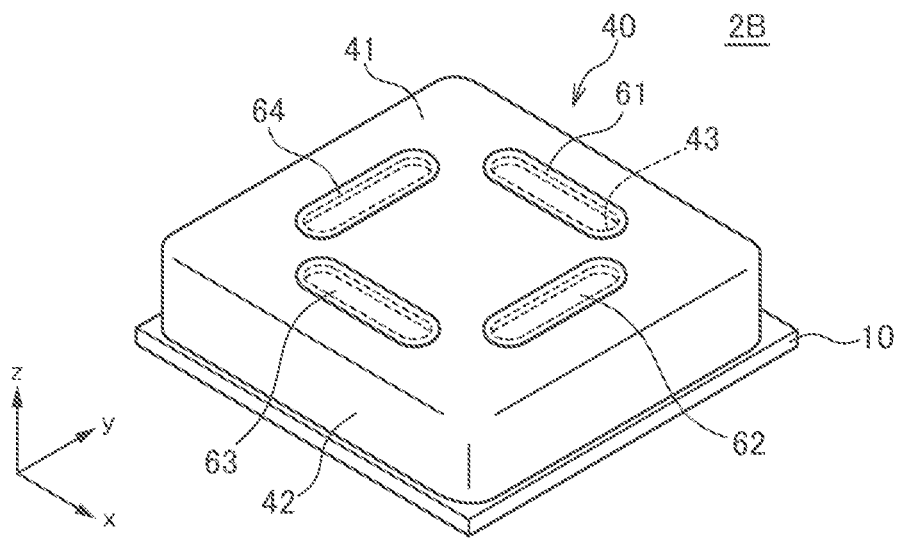
FIG. 11 is a schematic perspective view illustrating the outer appearances of sensor module 2B according to a sixth embodiment of the present invention.
Figure 12:
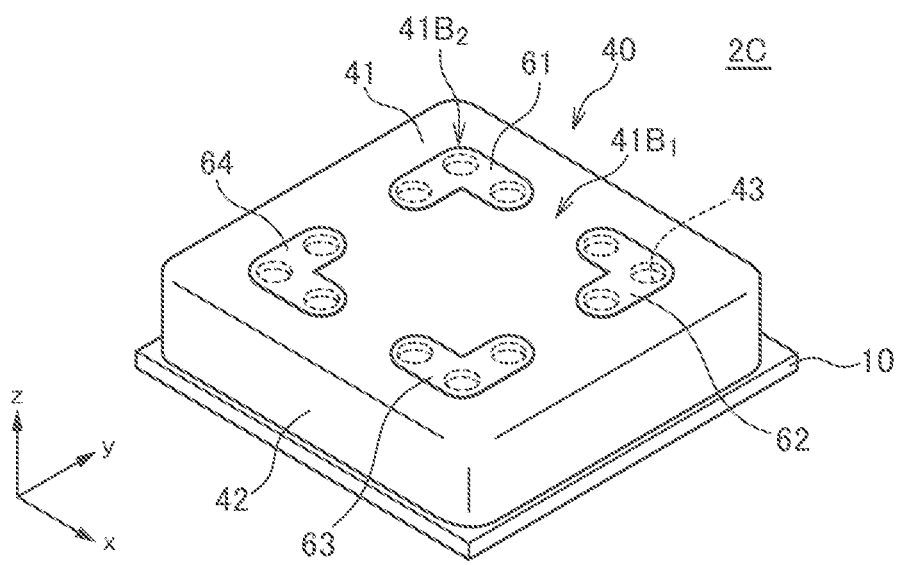
FIG. 12 is a schematic perspective view illustrating the outer appearances of sensor module 2C according to a seventh embodiment of the present invention.
Figure 13:
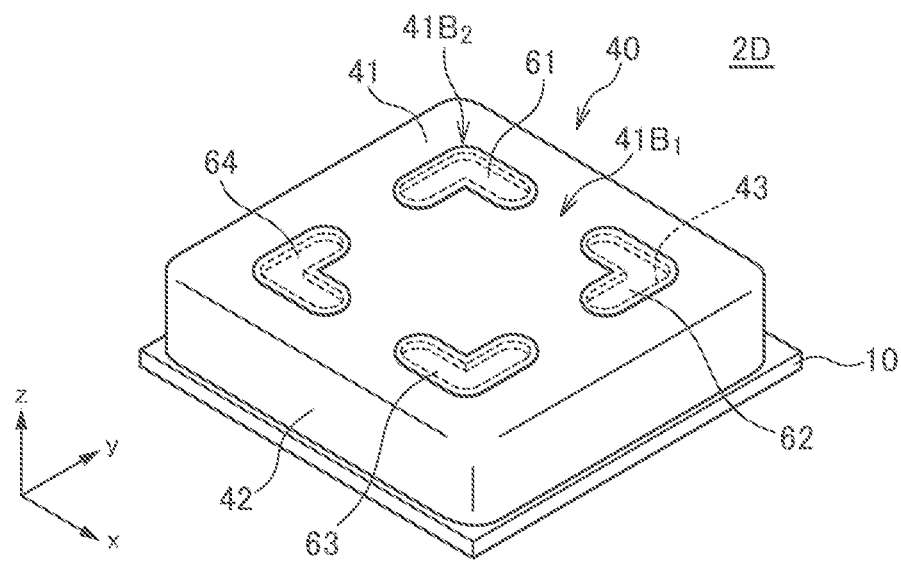
FIG. 13 is a schematic perspective view illustrating the outer appearances of sensor module 2D according to an eighth embodiment of the present invention.

FIG. 9 is a schematic perspective view illustrating the outer appearance of a sensor module 1D according to a fourth embodiment of the present invention.

The sensor module 1D illustrated in FIG. 9 differs from the sensor module 1C according to the third embodiment in that individual through holes 43 have an L-shape. Other configurations are the same as those of the sensor module 1C according to the third embodiment, so the same reference numerals are given to the same elements, and overlapping description will be omitted. Using the through holes 43 having such a shape allows greater circulation of air from outside to inside of the case 40.

Fifth to Eighth Embodiments

FIGS. 10 to 13 are schematic perspective views illustrating the outer appearances of sensor modules 2A to 2D according to fifth to eighth embodiments of the present invention.

The sensor modules 2A to 2D illustrated in FIGS. 10 to 13 differ respectively from the sensor modules 1A to 1D according to the first to fourth embodiments in that filters 61 to 64 are attached so as to overlap the through holes 43. Other configurations of the sensor modules 2A to 2D are the same respectively as those of the sensor modules 1A to 1D according to the first to fourth embodiments, so the same reference numerals are given to the same elements, and overlapping description will be omitted.

The filters 61 to 64 are each a member for preventing entering of a predetermined gas component that may deteriorate the sensor element, dust, and dirt. In the sensor modules 2A and 2B illustrated in FIGS. 10 and 11, the filters 61 to 64 are attached along the linear part $41B_1$ of the through hole formation area 41B. In the sensor modules 2C and 2D illustrated in FIGS. 12 and 13, the filters 61 to 64 are attached along the corner part $41B_2$ of the through hole formation area 41B. Since the filters 61 to 64 selectively cover the through hole formation area 41B without covering the center area 41A, the suction nozzle 50 of the chip mounter can avoid contacting the filters 61 to 64, thereby preventing the filters 61 to 64 from being damaged during a mounting process.

The filters 61 to 64 can be attached as follows. A filter sheet having cuts along which the filters 61 to 64 can be separated one from another is attached to the top plate part 41, and an unnecessary part of the filter sheet is removed so as to leave the filters 61 to 64 on the top plate part 41. This method can reduce the number of processes as compared to when the filters 61 to 64 are individually attached.

Ninth and Tenth Embodiments

Figure 14:
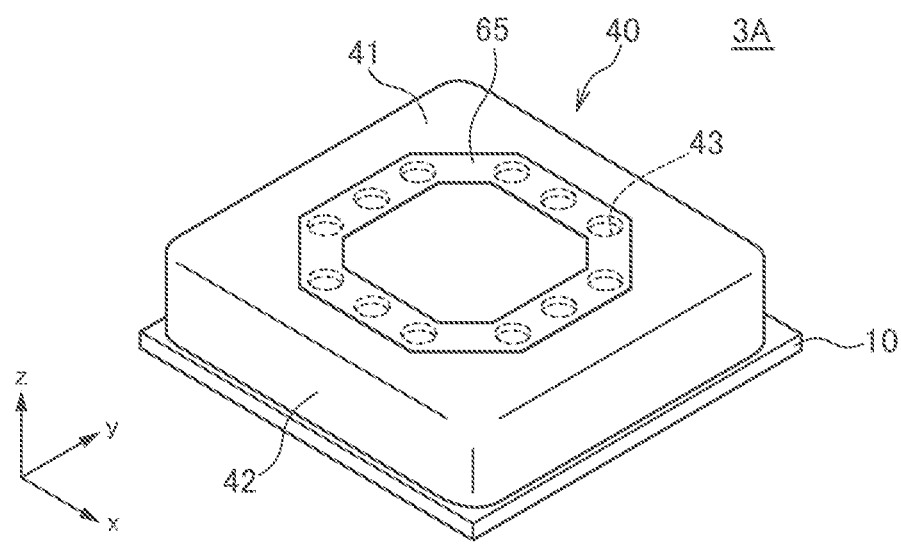
FIG. 14 is a schematic perspective view illustrating the outer appearances of sensor module 3A according to a ninth embodiment of the present invention.
Figure 15:
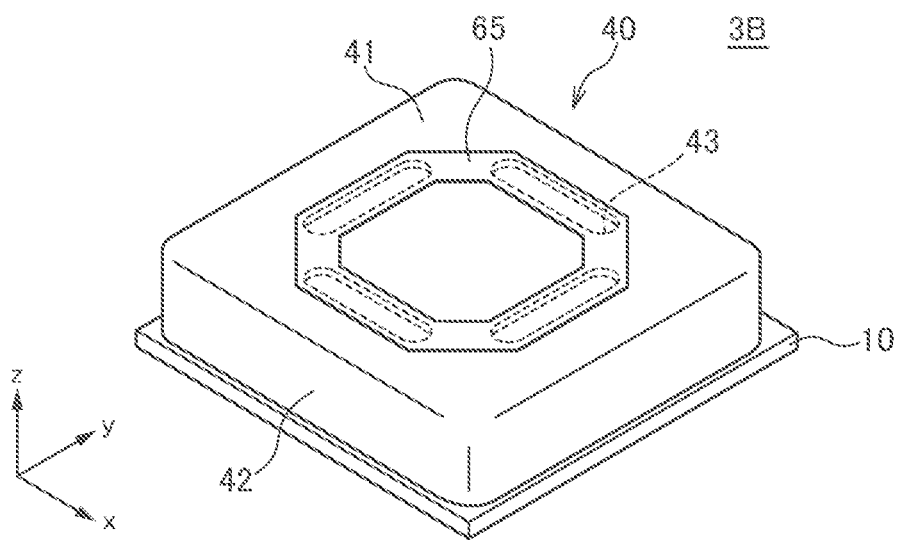
FIG. 15 is a schematic perspective view illustrating the outer appearances of sensor module 3B according to a tenth embodiment of the present invention.

FIGS. 14 and 15 are schematic perspective views illustrating the outer appearances of sensor modules 3A and 3B according to ninth and tenth embodiments of the present invention.

The sensor modules 3A and 3B illustrated in FIGS. 14 and 15 differ respectively from the sensor modules 2A and 2B according to the fifth and sixth embodiments in that a single ring-shaped filter 65 is used. Other configurations of the sensor modules 3A and 3B are the same respectively as those of the sensor modules 2A and 2B according to the fifth and sixth embodiments, so the same reference numerals are given to the same elements, and overlapping description will be omitted.

As exemplified in the ninth and tenth embodiments, the filter to be attached to the top plate part 41 may be a signal member having a continuous shape. In this case, attachment strength between the top plate part 41 and the filter can be enhanced due to an increase in the attachment area. To further enhance the attachment strength, the filter may be attached to the entire inner surface (the surface of the top plate part 41 that faces the surface 11 of the substrate 10). The outer and inner shapes of the filter 65 are each not a quadrangle, but an octagon so as to sufficiently separate the filter 65 from the corner portions of the top plate part 41. This can prevent contact between the jigs 51 to 54 and the filter 65 during the inspection process illustrated in FIG. 6.

The filter 65 can be attached as follows. A filter sheet having cuts is attached to the top plate part 41, and an unnecessary part of the filter sheet positioned in the center area 41A and an unnecessary part positioned in the outside area 41C are removed so as to leave the filter 65 on the top plate part 41.

Eleventh Embodiment

Figure 16:
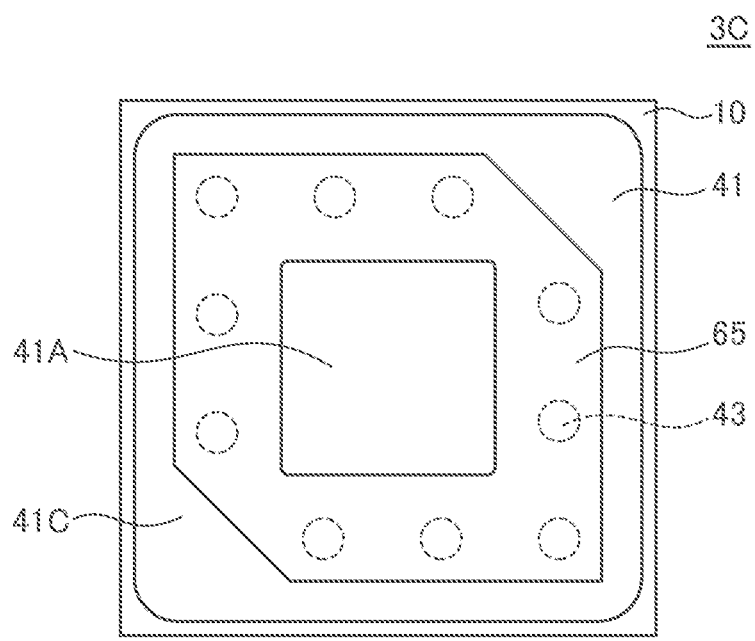
FIG. 16 is a schematic plan view illustrating the outer appearance of a sensor module 3C according to an eleventh embodiment of the present invention.

FIG. 16 is a schematic plan view illustrating the outer appearance of a sensor module 3C according to an eleventh embodiment of the present invention.

The sensor module 3C illustrated in FIG. 16 differs from the sensor module 3A according to the ninth embodiment in that the inner shape of the filter 65 is a quadrangle, and the outer shape thereof is a hexagon. Other configurations are the same as those of the sensor module 3A according to the ninth embodiment, so the same reference numerals are given to the same elements, and overlapping description will be omitted. As illustrated in FIG. 16, the filter 65 has a two-fold symmetric shape in which vicinities of the two diagonally facing corners of the top plate part 41 are cut. When the filter 65 having such a shape is used, the two jigs 52 and 53 which are positioned diagonally can be used in the inspection process illustrated in FIG. 6 so as not to contact the filter 65. Thus, the filter 65 need not be offset from the vicinities of all the four corners of the top plate part 41, but may be offset from the vicinities of only the two diagonally facing corners thereof.

Twelfth Embodiment

Figure 17:
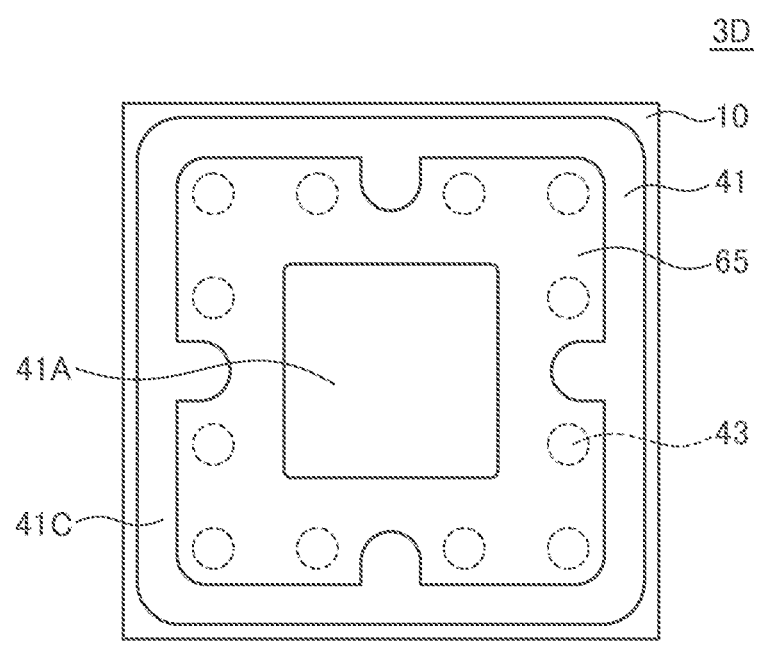
FIG. 17 is a schematic plan view illustrating the outer appearance of a sensor module 3D according to a twelfth embodiment of the present invention.

FIG. 17 is a schematic plan view illustrating the outer appearance of a sensor module 3D according to a twelfth embodiment of the present invention.

The sensor module 3D illustrated in FIG. 17 differs from the sensor module 3C according to the eleventh embodiment in that the filter 65 has a four-fold symmetric shape with a quadrangular outer shape and with the vicinity of substantially the center portion of each side of the top plate part 41 cut. Other configurations are the same as those of the sensor module 3C according to the eleventh embodiment, so the same reference numerals are given to the same elements, and overlapping description will be omitted. When the sensor module 3D according to the twelfth embodiment is inspected, the cut portions of the filter 65 are held with the jigs 51 to 54, whereby it is possible to perform the inspection while preventing closing of the through holes 43 and preventing contact between the jigs 51 to 54 and the filter 65.

Thirteenth Embodiment

Figure 18:
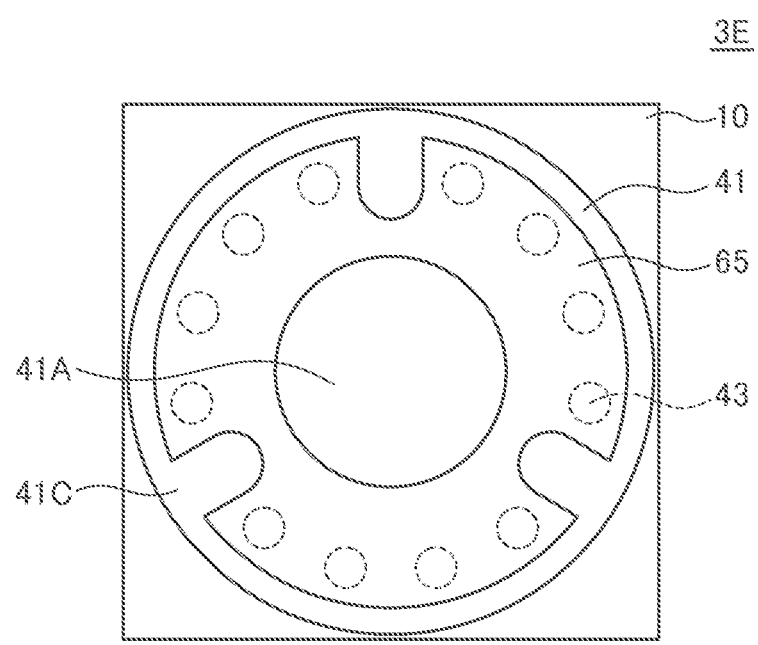
FIG. 18 is a schematic plan view illustrating the outer appearance of a sensor module 3E according to a thirteenth embodiment of the present invention.

FIG. 18 is a schematic plan view illustrating the outer appearance of a sensor module 3E according to a thirteenth embodiment of the present invention.

The sensor module 3E illustrated in FIG. 18 differs from the sensor modules 3A to 3D according to the ninth to twelfth embodiments in that the top plate part 41 of the case 40 has a circular shape and that the filter 65 has a three-fold symmetric shape. Other configurations are the same as those of the sensor modules 3A to 3D according to the ninth to twelfth embodiments, so the same reference numerals are given to the same elements, and overlapping description will be omitted. The filter 65 has three cuts. When the sensor module 3E is inspected, the three cut portions of the filter 65 are held with three jigs to fix the sensor module 3E. As exemplified in the present embodiment, the top plate part 41 of the case 40 may not necessarily have a rectangular shape in the present invention. Using the case 40 having the circular top plate part 41 can further enhance mechanical strength.

Fourteenth Embodiment

Figure 19:
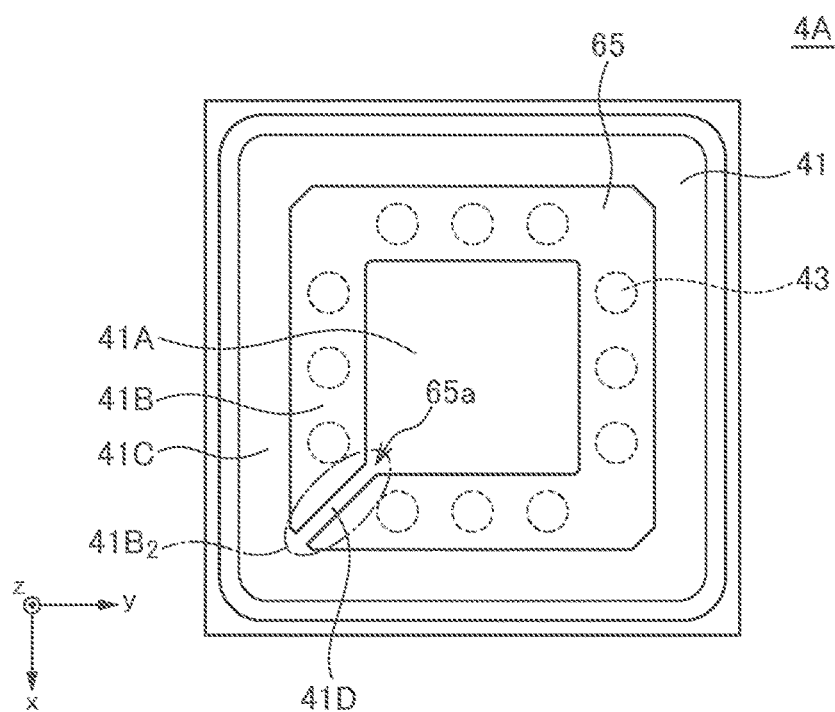
FIG. 19 is a schematic plan view illustrating the outer appearance of a sensor module 4A according to a fourteenth embodiment of the present invention.

FIG. 19 is a schematic plan view illustrating the outer appearance of a sensor module 4A according to a fourteenth embodiment of the present invention.

The sensor module 4A illustrated in FIG. 19 differs from the sensor module 3A according to the ninth embodiment in that the filter 65 has a separation part 65a. Other configurations are the same as those of the sensor module 3A according to the ninth embodiment, so the same reference numerals are given to the same elements, and overlapping description will be omitted. In the present embodiment, the separation part 65a is formed in the corner part 41B$_2$ of the through hole formation area 41B. Assuming that a part of the top plate part 41 that is covered with the filter 65 is referred to as "attachment area", most of the attachment area overlaps the through hole formation area 41B. On the other hand, assuming that a part of the top plate part 41 that is not covered with the filter 65 is referred to as "non-attachment area", the non-attachment area includes the center area 41A, outside area 41C, and a separation area 41D overlapping the through hole formation area 41B and connecting the center area 41A and the outside area 41C.

Figure 20:
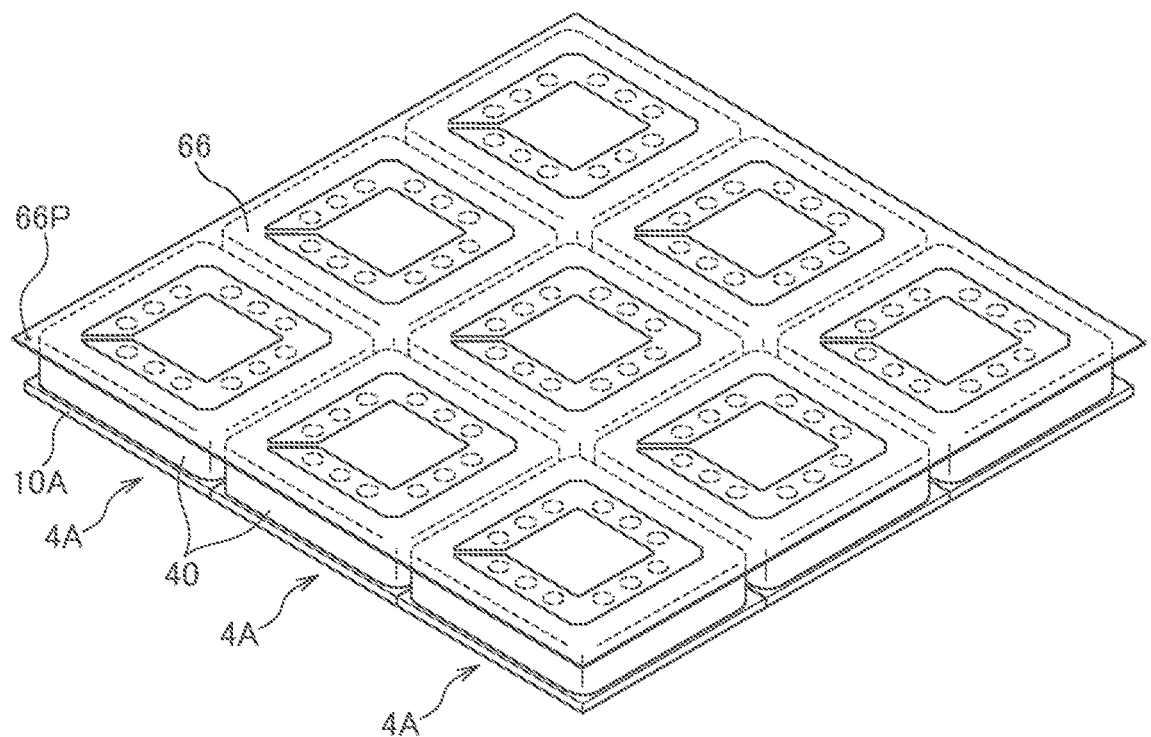
FIGS. 20 and 21 are schematic perspective views for explaining a part of the manufacturing process of the sensor module 4A according to the fourteenth embodiment.
Figure 21:
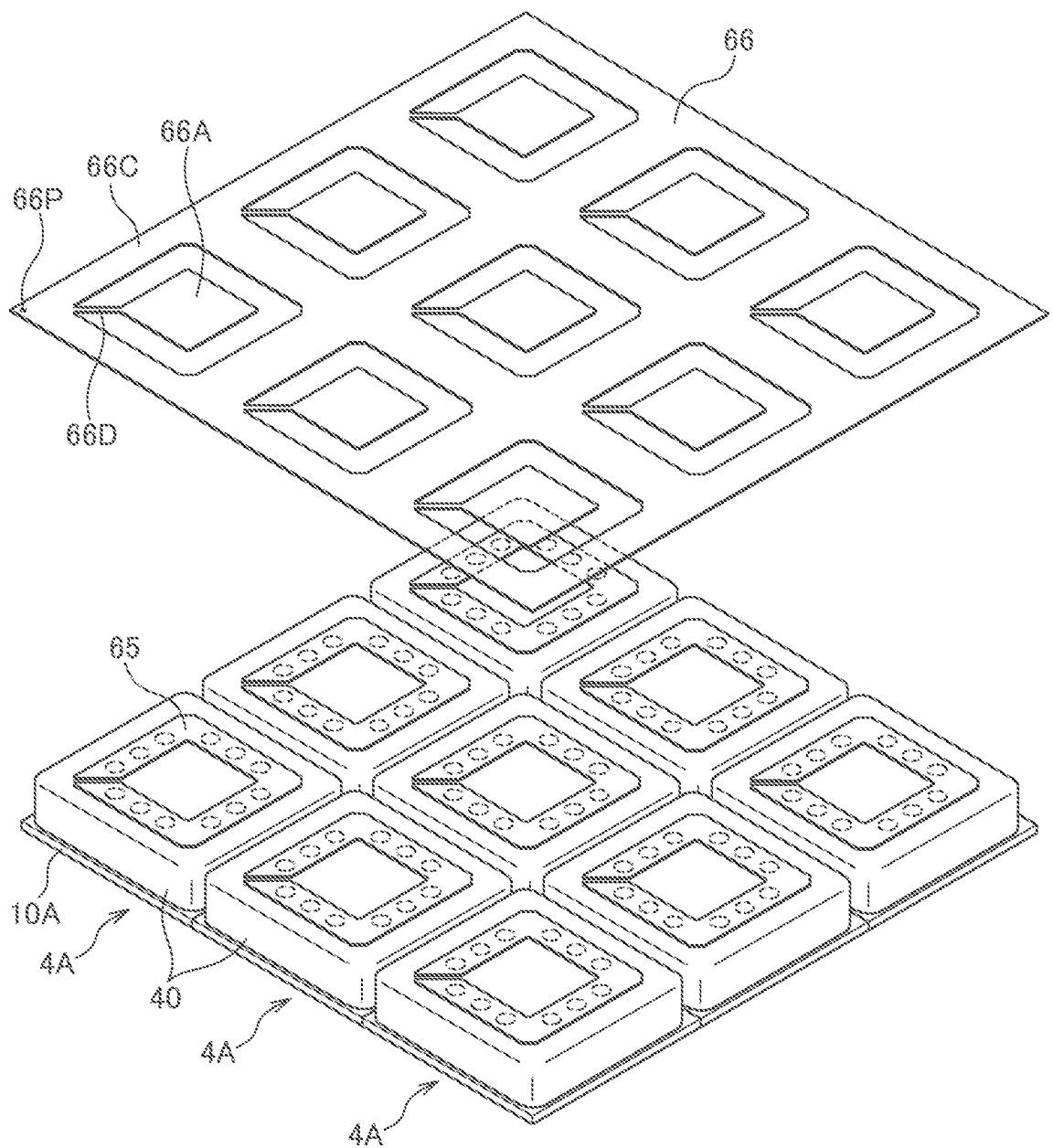

FIGS. 20 and 21 are schematic perspective views for explaining a part of the manufacturing process of the sensor module 4A according to the fourteenth embodiment.

First, as illustrated in FIG. 20, an aggregate substrate 10A mounted with a large number of the sensor chips 20 and control ICs 30 is prepared, and the cases 40 are fixed to positions corresponding to individual sensor modules 4A. In this state, a filter sheet 66 having a large area is attached to the plurality of cases 40. The filter sheet 66 has cuts, along which it can be separated into individual filters 65.

Then, as illustrated in FIG. 21, an unnecessary part of the filter sheet 66 is removed so as to leave the individual filters 65 on the cases 40. Specifically, upon the removal, the filter sheet 66 is lift starting from the separation area 41D side to separate the filters 65 from unnecessary parts 66A, 66C, and 66D. That is, a point 66P illustrated in FIGS. 20 and 21 is lifted. As a result, the unnecessary part 66C covering the outside area 41C, the unnecessary part 66D covering the separation area 41D, and the unnecessary part 66A covering the center area 41A are removed in this order, allowing all the unnecessary parts 66A, 66C, and 66D to be removed in a single removal step. Thereafter, the aggregate substrate 10A is diced into individual sensor modules 1A.

Figure 22A:
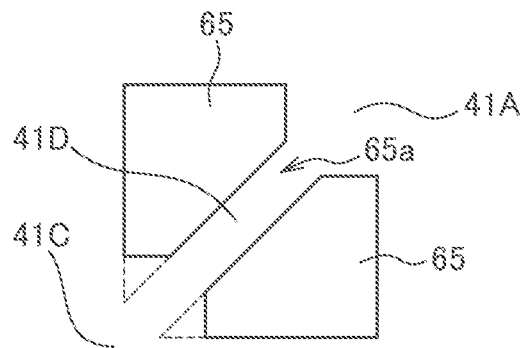
FIGS. 22A to 22C are schematic views for explaining examples in which the edge portion of the filter 65 is chamfered.
Figure 22B:
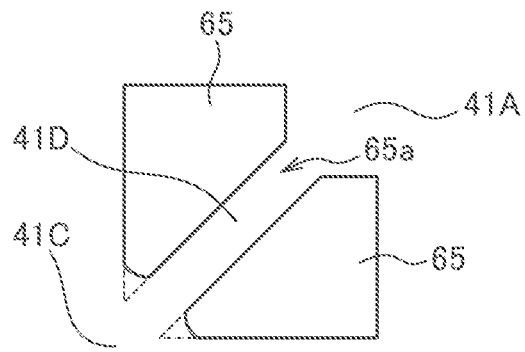
Figure 22C:
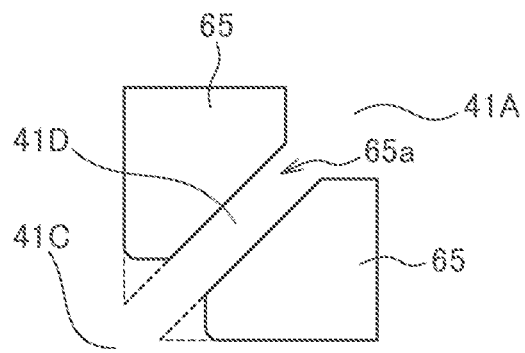

Thus, according to the sensor module 4A of the fourteenth embodiment, the removal process of the filter sheet 66 can be simplified. To prevent unintended peeling of the filter 65 during the removal process of the filter sheet 66, it is preferable to chamfer the edge portion of the filter 65 positioned at the boundary between the outside area 41C and the separation area 41D, as illustrated in FIGS. 22A to 22C. In the example illustrated in FIG. 22A, the edge portion of the filter 65 is linearly chamfered. In the example illustrated in FIG. 22B, the edge portion of the filter 65 is chamfered in a circular arc shape. In the example illustrated in FIG. 22C, the edge portion of the filter 65 is chamfered in a linear shape, and the resultant corner portion is further chamfered in a circular arc shape. The dashed line in FIGS. 22A to 22C denotes the chamfered portion.

Figure 23A:
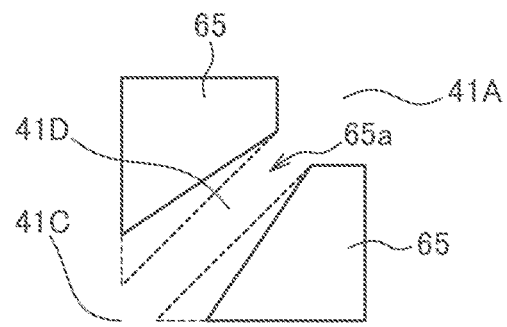
FIGS. 23A and 23B are schematic views for explaining examples in which the width of the separation area 41D becomes wider from the center area 41A toward the outside area 41C.
Figure 23B:
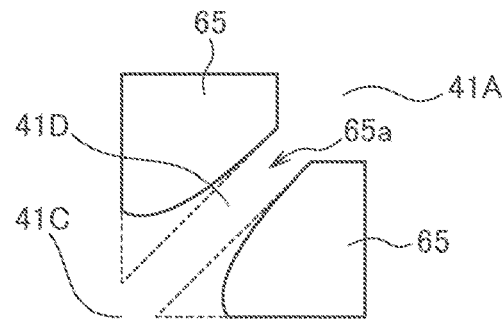

To facilitate the removal of the unnecessary part 66D, it is preferable to make the width of the separation area 41D wider from the center area 41A toward the outside area 41C, as illustrated in FIGS. 23A and 23B. In the example illustrated in FIG. 23A, the width of the separation area 41D becomes continuously wider from the center area 41A toward the outside area 41C. In the example illustrated in FIG. 23B, the edge portion of the filter 65 is largely chamfered in a circular arc shape, whereby the width of the separation area 41D is locally enlarged in the vicinity of the outside area 41C. The dashed line in FIGS. 23A and 23B denotes the position of the separation area 41D before being enlarged in width.

Fifteenth Embodiment

Figure 24:
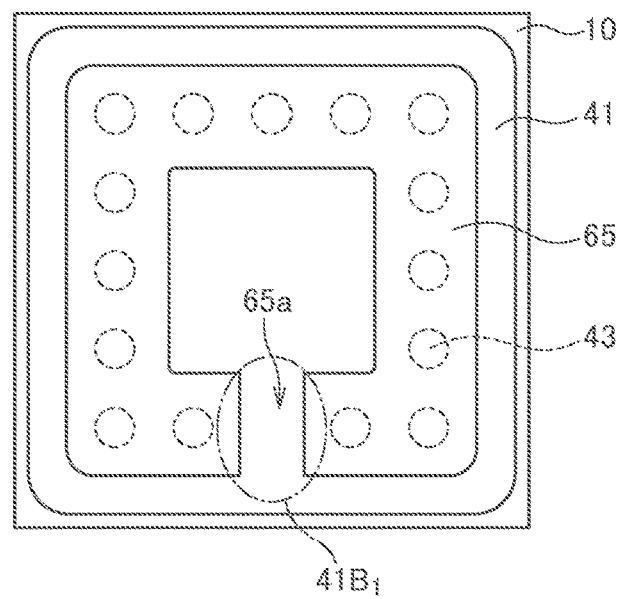
FIG. 24 is a schematic plan view illustrating the outer appearance of a sensor module 4B according to a fifteenth embodiment of the present invention.

FIG. 24 is a schematic plan view illustrating the outer appearance of a sensor module 4B according to a fifteenth embodiment of the present invention.

The sensor module 4B illustrated in FIG. 24 differs from the sensor module 4A according to the fourteenth embodiment in that the separation part 65a of the filter 65 is formed in the linear part $41B_1$ of the through hole formation area 41B. Other configurations are the same as those of the sensor module 4A according to the fourteenth embodiment, so the same reference numerals are given to the same elements, and overlapping description will be omitted. As exemplified in the present embodiment, the separation part 65a of the filter 65 may not necessarily be formed in the corner part $41B_2$.

Figure 25A:
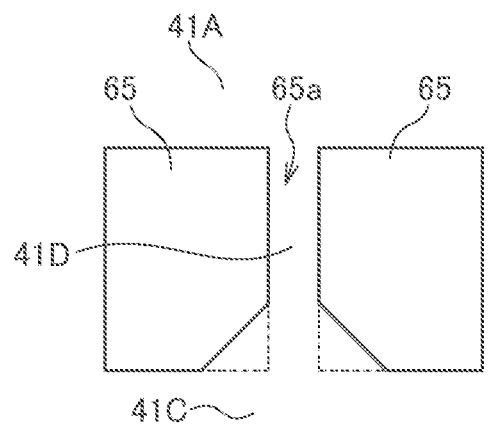
FIGS. 25A to 25C are schematic views for explaining examples in which the edge portion of the filter 65 is chamfered.
Figure 25B:
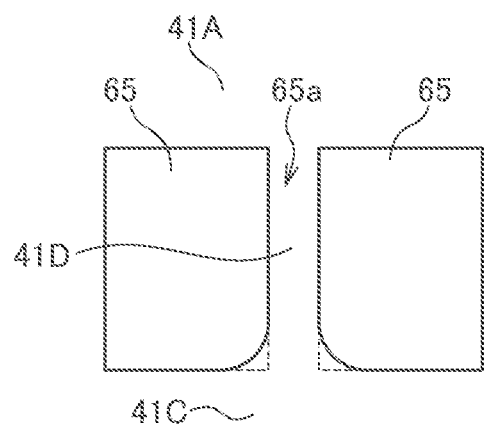
Figure 25C:
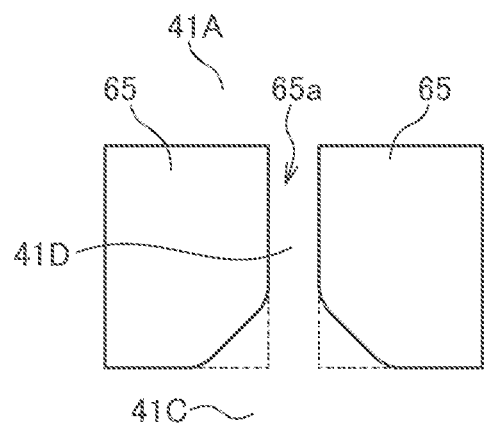

To prevent unintended peeling of the filter 65 in the removal process of the filter sheet 66, it is preferable to chamfer the edge portion of the filter 65 positioned at the boundary between the outside area 41C and the separation area 41D, as illustrated in FIGS. 25A to 25C. In the example illustrated in FIG. 25A, the edge portion of the filter 65 is linearly chamfered. In the example illustrated in FIG. 25B, the edge portion of the filter 65 is chamfered in a circular arc shape. In the example illustrated in FIG. 25C, the edge portion of the filter 65 is chamfered in a linear shape, and the resultant corner portion is further chamfered in a circular arc shape. The dashed line in FIGS. 25A to 25C denotes the chamfered portion.

Figure 26A:
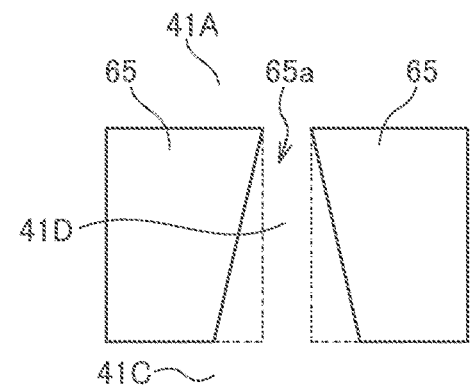
FIGS. 26A and 26B are schematic views for explaining examples in which the width of the separation area 41D becomes wider from the center area 41A toward the outside area 41C.
Figure 26B:
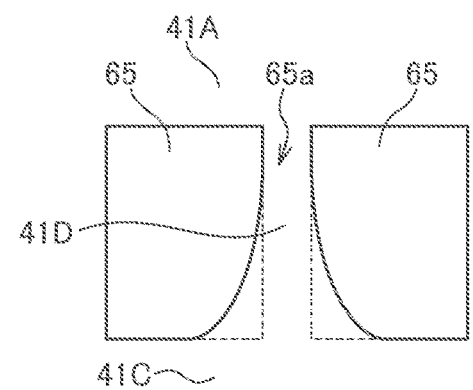

To facilitate the removal of unnecessary part 66D, it is preferable to make the width of the separation area 41D wider from the center area 41A toward the outside area 41C, as illustrated in FIGS. 26A and 26B. In the example illustrated in FIG. 26A, the width of the separation area 41D becomes continuously wider from the center area 41A toward the outside area 41C. In the example illustrated in FIG. 26B, the edge portion of the filter 65 is largely chamfered in a circular arc shape, whereby the width of the separation area 41D is locally enlarged in the vicinity of the outside area 41C. The dashed line in FIGS. 26A and 26B denotes the position of the separation area 41D before being enlarged in width.

Sixteenth Embodiment

Figure 27:
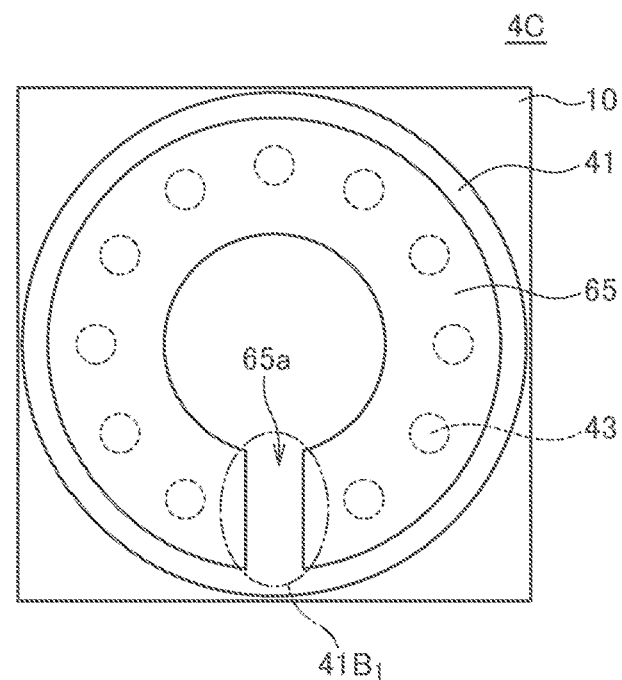
FIG. 27 is a schematic plan view illustrating the outer appearance of a sensor module 4C according to a sixteenth embodiment of the present invention.

FIG. 27 is a schematic plan view illustrating the outer appearance of a sensor module 4C according to a sixteenth embodiment of the present invention.

The sensor module 4C illustrated in FIG. 27 differs from the sensor module 4B according to the fifteenth embodiment in that the top plate part 41 of the case 40 has a circular shape. Other configurations are the same as those of the sensor module 4B according to the fifteenth embodiment, so the same reference numerals are given to the same elements, and overlapping description will be omitted. As exemplified in the present embodiment, the top plate part 41 of the case 40 may not necessarily have a rectangular shape in the present invention. Using the case 40 having the circular top plate part 41 can further enhance mechanical strength.

It is apparent that the present invention is not limited to the above embodiments, but may be modified and changed without departing from the scope and spirit of the invention.

What is claimed is:

1. A sensor module comprising:
   a substrate having a top surface and a back surface;
   a sensor element mounted on the top surface of the substrate;
   an external terminal formed on the back surface of the substrate; and
   a case fixed to the substrate so as to cover the sensor element,
   wherein the case has a top plate part having a first plurality of through holes and a second plurality of through holes,
   wherein the top plate part has a center area having no through holes, a first through hole formation area having the first plurality of through holes, and a second through hole formation area having the second plurality of through holes,
   wherein the center area is positioned between the first and second through hole formation areas in a first direction,
   wherein the sensor module further comprises a filter overlapping the first and second plurality of through holes, and
   wherein the filter selectively covers the first and second through hole formation areas so as to overlap the first and second plurality of through holes without covering the center area.

2. The sensor module as claimed in claim 1, wherein the top plate part has a rectangular outer shape.

3. The sensor module as claimed in claim 1, wherein the filter is formed as a single member having a continuous shape.

4. The sensor module as claimed in claim 1, wherein each of the first and second plurality of through holes are arranged in a second direction perpendicular to the first direction.

5. The sensor module as claimed in claim 1, wherein a number of each of the first and second plurality of through holes is more than two.

6. The sensor module as claimed in claim 1,
wherein the top plate part further has a third plurality of through holes located at a third through hole formation area, and a fourth plurality of through holes located at a fourth through hole formation area, and
wherein the center area is positioned between the third and fourth through hole formation areas in a second direction perpendicular to the first direction such that the center area is surrounded by the first, second, third, and fourth through hole formation areas.

7. The sensor module as claimed in claim 6,
wherein each of the first and second plurality of through holes are arranged in the second direction, and
wherein each of the third and fourth plurality of through holes are arranged in the first direction.

8. The sensor module as claimed in claim 6, wherein a number of each of the first, second, third, and fourth plurality of through holes is more than two.

9. The sensor module as claimed in claim 6, wherein the filter covers the first, second, third, and fourth through hole formation areas so as to overlap the first, second, third, and fourth plurality of through holes without covering the center area.

10. The sensor module as claimed in claim 9, wherein the filter is formed as a single member having a continuous shape.

11. The sensor module as claimed in claim 9, wherein the filter is ring-shaped so as to surround the center area.

12. The sensor module as claimed in claim 9,
wherein the top plate part further has:
an outside area positioned outside the first, second, third, and fourth through hole formation areas so as to surround the first, second, third, and fourth through hole formation areas; and
a separation area located between the first and third through hole formation areas so as to connect the center area with the outside area, and wherein the center area, outside area, and separation area are free from the filter.

13. The sensor module as claimed in claim 1,
wherein the top plate part of the case has an inner surface facing the top surface of the substrate and an outer surface located on a side opposite to the inner surface, and
wherein the filter is attached on the outer surface.

14. A sensor module comprising:
a substrate having a top surface and a back surface;
a sensor element mounted on the top surface of the substrate;
an external terminal formed on the back surface of the substrate;
a case fixed to the substrate so as to cover the sensor element, the case including a top plate part having an inner surface facing the top surface of the substrate, an outer surface located on a side opposite to the inner surface, and a plurality of through holes; and
a filter is attached on the outer surface of the top plate part so as to cover the plurality of through holes,
wherein the plurality of through holes includes first and second through holes,
wherein the outer surface of the top plate part has a center area having no through holes and located between the first and second through holes in a first direction, and
wherein the filter selectively covers the first and second through holes without covering the center area.

15. The sensor module as claimed in claim 14,
wherein the plurality of through holes further includes third and fourth through holes,
wherein the center area is located between the third and fourth through holes in a second direction perpendicular to the first direction, and
wherein the filter selectively covers the first, second, third, and fourth through holes without covering the center area.

16. The sensor module as claimed in claim 15,
wherein a width of each of the first and second through holes in the second direction is greater than a width of each of the first and second through holes in the first direction, and
wherein a width of each of the third and fourth through holes in the first direction is greater than a width of each of the third and fourth through holes in the second direction.

17. A sensor module comprising:
a substrate having a top surface;
a sensor element mounted on the top surface of the substrate;
a case fixed to the substrate so as to cover the sensor element, the case including a top plate part having an inner surface facing the top surface of the substrate, an outer surface located on a side opposite to the inner surface, and a plurality of through holes; and
a filter is attached on the outer surface of the top plate part so as to cover the plurality of through holes,
wherein the filter is formed as a single member having a continuous shape,
wherein the outer surface of the top plate part has a center area having no through holes, a through hole formation area having the plurality of through holes and surrounding the center area, an outside area surrounding the through hole formation area, and a separation area located so as to connect the center area with the outside area, and
wherein the filter selectively covers the through hole formation area without covering the center area, outside area, and separation area.

18. The sensor module as claimed in claim 17, wherein a width of the separation area wider from the center area toward the outside area.

* * * * *